(12) United States Patent
Karavas et al.

(10) Patent No.: US 10,894,026 B2
(45) Date of Patent: Jan. 19, 2021

(54) PHARMACEUTICAL COMPOSITIONS COMPRISING A FUMARIC ACID ESTER AND METHOD FOR THE PREPARATION THEREOF

(71) Applicant: PHARMATHEN S.A., Pallini-Attikis (GR)

(72) Inventors: Evangelos Karavas, Pallini Attikis (GR); Efthymios Koutris, Pallini Attikis (GR); Vasiliki Samara, Pallini Attikis (GR); Ioanna Koutri, Pallini Attikis (GR); Anastasia Kalaskani, Pallini Attikis (GR); Morfis Abatzis, Pallini Attikis (GR); Manolis Fousteris, Pallini Attikis (GR)

(73) Assignee: PHARMATHEN S.A., Attikis (GR)

( * ) Notice: Subject to any disclaimer, the term of this patent is extended or adjusted under 35 U.S.C. 154(b) by 22 days.

(21) Appl. No.: 16/339,281

(22) PCT Filed: Oct. 25, 2017

(86) PCT No.: PCT/EP2017/025317
§ 371 (c)(1),
(2) Date: Apr. 3, 2019

(87) PCT Pub. No.: WO2018/077479
PCT Pub. Date: May 3, 2018

(65) Prior Publication Data
US 2020/0046670 A1   Feb. 13, 2020

(30) Foreign Application Priority Data

Oct. 25, 2016   (GR) ............................... 20160100551
Oct. 25, 2017   (WO) ................. PCT/EP2017/025317

(51) Int. Cl.
*A61K 31/225*   (2006.01)
*A61K 9/20*   (2006.01)
*A61K 9/28*   (2006.01)
*A61K 9/48*   (2006.01)

(52) U.S. Cl.
CPC .......... *A61K 31/225* (2013.01); *A61K 9/2009* (2013.01); *A61K 9/2054* (2013.01); *A61K 9/2095* (2013.01); *A61K 9/2846* (2013.01); *A61K 9/2886* (2013.01); *A61K 9/4825* (2013.01)

(58) Field of Classification Search
None
See application file for complete search history.

(56) References Cited

FOREIGN PATENT DOCUMENTS

| | | |
|---|---|---|
| CN | 104027311 A | 9/2014 |
| CN | 104352441 A | 2/2015 |
| CN | 104971048 A | 10/2015 |
| WO | 98/32426 A1 | 7/1998 |
| WO | 2010079222 A1 | 7/2010 |
| WO | 2015028473 A1 | 3/2015 |

OTHER PUBLICATIONS

Machine translation, CN 104352441 (Year: 2015).*
Machine translation, CN 104027311 (Year: 2011).*
Written Opinion of the ISR for PCT/EP2017/025317.

* cited by examiner

*Primary Examiner* — Bethany P Barham
*Assistant Examiner* — Barbara S Frazier
(74) *Attorney, Agent, or Firm* — AKC Patents, LLC; Aliki K. Collins

(57) ABSTRACT

The present invention relates to a delayed release pharmaceutical composition comprising a fumaric acid ester such as Dimethyl fumarate in the form of gastro-resistant tablets filled into hard gelation capsule.

10 Claims, No Drawings

PHARMACEUTICAL COMPOSITIONS COMPRISING A FUMARIC ACID ESTER AND METHOD FOR THE PREPARATION THEREOF

TECHNICAL FIELD OF THE INVENTION

The present invention relates to pharmaceutical formulations of fumaric acid esters such as Dimethyl fumarate in the form of enteric coated tablets filled into hard gelatin capsule and a method for the preparation thereof.

BACKGROUND OF THE INVENTION

Multiple sclerosis (MS) shares an immune-mediated origin with psoriasis. Long-term safety and efficacy data generated in Europe from usage of fumaric acid formulations in the latter disease constituted grounds to investigate their effects in MS patients.

MS is thought to be a disease of the immune system that is characterized by infiltration into the central nervous system of autoreactive immune cells; these, with varying degrees of severity, cause demyelination, gliosis, neuronal loss and eventually cerebral atrophy.

Dimethyl fumarate belongs to a class of medications called Nrf2 activators. It may work by decreasing inflammation and preventing nerve damage that may cause symptoms of multiple sclerosis. The mechanism of action of Dimethyl fumarate in multiple sclerosis is not well understood. It is thought to involve Dimethyl fumarate degradation to its active metabolite monomethyl fumarate (MMF) then MMF up-regulates the Nuclear factor (erythroid-derived 2)-like 2 (Nrf2) pathway that is activated in response to oxidative stress.

Dimethyl fumarate is designated chemically as (E)-2-butenedioic acid dimethyl ester and its molecular formula is $C_6H_8O_4$ corresponding to a molecular weight of 144.13. It is a white to off-white powder that is insoluble in water and sparingly soluble in methanol.

EP-A-2564839 discloses a pharmaceutical formulation comprising an erosion matrix comprising one or more fumaric acid esters as well as one or more rate-controlling agents, wherein erosion of said erosion matrix permits controlled release of said fumaric acid ester(s).

WO-A-2015/042294 discloses nanoparticle compositions of dimethyl fumarate.

U.S. Pat. No. 6,509,376 discloses pharmaceutical compositions of dialkyl fumarates in the form of enteric coated micro-tablets or micro-pellets wherein the size of such units is less than 5000 microns.

Although each of the patents above represents an attempt to provide dosage forms for the controlled delivery of Dimethyl fumarate, an improvement in the matter is still desirable.

SUMMARY OF THE INVENTION

It is, therefore, an object of the present invention to provide a stable oral solid dosage formulation for oral administration containing a fumaric acid ester and in particular Dimethyl fumarate, as an active ingredient, which overcomes the deficiencies of the prior art and also avoids sublimation of the drug providing a uniform and constant rate of release over an extended period of time.

It is another object of the present invention to provide a delayed release pharmaceutical composition for oral administration comprising Dimethyl fumarate as an active ingredient, which is bioavailable, with sufficient self-life and good pharmacotechnical properties.

A major object of the present invention is the selection of two gastro-resistant polymeric layers in order to achieve a delayed drug release profile.

An essential object of the present invention is to define the optimum particle size of Dimethyl fumarate to reach a dissolution profile of desirable pharmacokinetics.

As drug release from hydrophilic matrix tablets can be strongly influenced by the dimensions of tablets, it is essential object of the present invention to identify the optimum tablet diameter.

In accordance with the above objects of the present invention tablets coated with two gastro-resistant polymeric layers filled into hard gelatin capsule are provided in order to obtain delayed release profile of the drug.

A further approach of the present invention is to provide a delayed release dosage form containing Dimethyl fumarate which is manufactured through a fast, simple and cost-effective process.

According to another embodiment of the present invention, a process for the preparation of a modified release pharmaceutical composition of Dimethyl fumarate for oral administration comprising two gastro-resistant polymeric layers is provided, which comprises the following steps:

Dimethyl fumarate is blended with excipients of core tablet;

The obtained powder mixture is pressed into round convex tablets of about 6 mm;

The first coating solution is sprayed onto the tablet cores up to the desired weight gain;

The second coating solution is sprayed onto the coated tablets up to the desired weight gain;

The enteric coated tablets are filled into hard gelatin capsules.

Other objects and advantages of the present invention will become apparent to those skilled in the art in view of the following detailed description.

DETAILED DESCRIPTION OF THE INVENTION

For the purposes of the present invention, a pharmaceutical composition comprising an active ingredient (e.g. Dimethyl fumarate) is considered to be "stable" if said ingredient degrades less or more slowly than it does on its own and/or in known pharmaceutical compositions.

It is well-known that dialkyl fumarates, e.g. Dimethyl fumarate, sublimate at relatively low temperatures. Thus, it is desirable to develop a medicament comprising Dimethyl fumarate which will have less sublimation problem during production and storage of the composition. The problem of sublimation is solved by coating core tablet(s) of Dimethyl fumarate by at least one layer comprising a pharmaceutically acceptable polymer. The aqueous solubility and degradation of the polymer is dependent on pH. The coating process in case of more than one coating layers is performed in two stages. The first (innermost) coating layer is applied on the core in a temperature not exceeding 40° C., preferably not exceeding 30° C. The subsequent second coating layer may be applied at any conventionally used temperature including temperature exceeding 40° C., as the Dimethyl fumarate particles have already been sufficiently protected against sublimation by the first layer of the polymer.

The first polymeric coating protects core tablet matrix from any environmental reason that can cause degradation including the second coating layer which can be in the form of an aqueous suspension that may cause API hydrolysis upon contact. When API gets hydrolyzed, the active metabolite MMF is produced. MMF is a primary degradation product of the final drug product.

Dimethyl fumarate core tablet is coated with two pH-dependent entero-resistant polymeric layers. A polymer is "pH-dependent entero-resistant" if the coating layer comprising it does not allow acidic gastric water to penetrate through but it allows the penetration of water to the Dimethyl fumarate core (e.g., by dissolution, swelling, degradation etc.) at the essentially neutral pH of the intestines. In particular, a pH-dependent entero-resistant polymer suitable for purposes of the present invention is a polymer which dissolves, swells or degrades at a pH of 4.5 or higher, preferably pH 5.0 or higher. In a typical embodiment, the polymer dissolves, swells or degrades at a pH in the range of from 4.5 to 7.0, preferably from 5.0 to 6.5.

Non-limiting examples of suitable pH-dependent entero-resistant polymers useful as the coating material for purpose of the present invention include, alone or in combination, polymethacrylates, hydroxypropyl methyl cellulose acetate succinate (HPMC-AS), hydroxypropyl methyl cellulose phthalate (HPMCP), polyvinyl acetate phthalate (PVAP), cellulose acetate phthalate (CAP) and shellac.

The preferred pH-dependent entero-resistant polymer in the present invention is the polymethacrylate polymer, more preferably a copolymer of methacrylic acid and methyl methacrylate and a copolymer of methacrylic acid and ethyl acrylate.

In accordance with the present invention the pH-dependent enteric coating allows for a controlled release of the active pharmaceutical ingredient in the gastrointestinal tract. In particular, the release of the active substance in the stomach environment is minimized, whereby the majority of the amount of Dimethyl fumarate is released in the intestines. The desired release rate in the intestines may be modulated by choosing the right combination of coating polymer(s), relative thickness of the coating layer surrounding the Dimethyl fumarate core and, optionally, by the inclusion of other excipients known to modify the release of the active substance.

pH-dependent entero-resistant polymer of the first coating layer is present in the preferred composition of the present invention in an amount of 1-5% (w/w) of the composition. Most preferably, pH-dependent entero-resistant polymer in the first coating layer is a methacrylic acid methyl methacrylate polymer.

pH-dependent entero-resistant polymer of the second coating layer is present in the preferred composition of the present invention in an amount of 15-25% (w/w) of the composition. Most preferably, pH-dependent entero-resistant polymer in the second coating layer is a methacrylic acid ethyl acrylate polymer.

Apart from the pharmaceutically acceptable pH-dependent entero-resistant polymer, the coating may comprise other functional excipients, e.g. plasticizers, anti-tacking agents, pH adjustors, stabilizers, pore formers or additives improving the moisture/oxygen barrier, as known in the art.

According to the present invention weight gain of 4-8% w/w, most preferably 6% w/w on the first enteric coating was the optimum level in order to protect the API from hydrolysis issues upon contact with the second polymeric coating layer (aqueous suspension). It also provided a desirable acid resistance when combing with the second enteric coating. Talc level on first enteric coating solution is 2-6% w/w, most preferably 4 to 5% w/w.

According to the present invention the optimum weight gain of second enteric coating is 5-15%, most preferably 10% w/w. Talc level on second enteric coating solution is 2-6% w/w, most preferably 5% w/w.

Dimethyl fumarate is comprised in the preferred composition of the present invention in an amount of 60-70% w/w of core tablet.

According to the desired properties of the composition, any number of ingredients may be selected to form the core of the composition, alone or in combination, based upon their known uses in preparation of solid dosage form compositions.

Such ingredients may include, but are not limited to, diluents, binders, disintegrants, glidants, and lubricants. Any optional excipients must be compatible with the active substance so that it does not interfere with it in the composition.

Diluents may be, for example, calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, mannitol, maltose, maltitol.

Binders may be, for example, acacia mucilage, alginic acid, carbomer, carboxymethylcellulose calcium, carboxymethylcellulose sodium, microcrystalline cellulose, powdered cellulose, ethyl cellulose, gelatin, liquid glucose, guar gum, hydroxyethyl cellulose, hydroxypropyl cellulose, hydroxypropylmethyl cellulose, maltodextrin, methylcellulose, polydextrose, polyethylene oxide, povidone, sodium alginate, starch paste, pregelatinized starch and sucrose.

Disintegrants may be, for example, alginic acid, carbon dioxide, carboxymethylcellulose calcium, carboxymethylcellulose sodium, microcrystalline cellulose, powdered cellulose, croscarmellose sodium, crospovidone, sodium docusate, guar gum, hydroxypropyl cellulose, methylcellulose, polacrilin potassium, poloxamer, povidone, sodium alginate, sodium glycine carbonate, sodium lauryl sulfate, sodium starch glycolate, starch, pregelatinized starch.

Glidants may be, for example, powdered cellulose, starch, talc, silica colloidal anhydrous.

Lubricants may be selected from magnesium stearate, polyethylene glycol 4000, polyethylene glycol 6000, sodium lauryl sulfate, starch, talc.

The optimum particle size distribution of Dimethyl fumarate according to the present invention is D(50)=50-150 microns and D(90)=200-300 microns, most preferably D(90) is less than 300 microns. Particle sizes may be measured using various commonly used techniques such as laser light diffraction.

Multiple unit dosage forms (MUDFs) are characterized by the fact that the dose is administered as a number of subunits, each single unit containing the drug. The overall dose is then, the sum of the quantity of the drug in each subunit, and the functionality of the entire dose is directly related to the functionality of the individual subunit.

Tableting was the chosen production method because it is faster, easier, adds fewer steps to the process and is the most economical. Further, the tableting method ensures a high production yield, contrary to the manufacture of pellets where the loss of production output is usually much higher. Furthermore, multi-particulate systems are extremely complex to produce, requiring large numbers of excipients and multiple manufacturing steps. Extrusion-spheronization technique which is the common pellet manufacturing process requires a large quantity of liquid binder to achieve a plastic wet mass. The risk of an accidental high dosage due to possible cracking of coating or not uniform coating of the particulates of multi particular dosage forms is eliminated. Consequently, according to the present invention the finished dosage form is in the form of enteric coated tablets inside a hard gelatin capsule.

Based on dissolution data coated tablets of higher size (e.g approximately 6 mm), show lower drug release rate than tablets of smaller size such as in the marketed product. The preferred composition of the present invention is bioequivalent with marketed product but due to the tablets' higher size shows slower drug release and thus drug level is more uniform within the therapeutic range.

Tablets of smaller size have many advantages over single unit dosage forms. They can be manufactured relatively easily, they offer flexibility during the formulation development; they have excellent size uniformity, regular shape and a smooth surface, thereby act as an excellent coating substrate; they have less risk of dose dumping; they have less inter and intra-subject variability, they offer high degree of dispersion in the GI tract, thus minimizing the risks of high local drug concentrations; they offer high drug loading, a wide range of release rate patterns and also fine tuning of these release rates. Such advantages apply to the present invention's tablets that have a size 5-10 mm, most preferably 6 mm.

Gastro-resistant delayed-release capsules were chosen as the pharmaceutical dosage form in the present product development. Hard gelatin capsules are widely used because a) swallowing is very easy, b) the shells have no taste and the drugs which are not having pleasant taste and smell can be administered, c) they can be manufactured in different colors and d) the drug will be released easily as there is no compaction When it comes to a decision which dosage form will be developed for the market, high production costs of hard gelatin capsule products are generally assumed. This assumption is valid if the production costs are limited to the comparison of the excipient costs only. When taking into account the total manufacturing costs, which include the hidden costs coming from process equipment, GMP space required, total production time, in-process controls, analytical, cleaning and validation work the comparison easily turns out in favor of the capsule formulation.

EXAMPLES

Example 1

TABLE 1

Composition 1

| Core tablet | Component | |
|---|---|---|
| | mg per tablet | mg per capsule |
| Dimethyl Fumarate | 60 | 240 |
| Microcrystalline cellulose | 27 | 108 |
| Croscarmellose Sodium | 4.5 | 18 |
| Magnesium Stearate | 0.462 | 1.848 |
| Colloidal Silicon Dioxide | 0.462 | 1.848 |
| Total weight for uncoated tablet | 92.425 | 369.700 |

Uncoated compositions (composition 1) as presented in table 1 above were prepared according to the following manufacturing process:
  Dimethyl fumarate was blended with croscarmellose sodium, microcrystalline cellulose and colloidal silicon dioxide;
  The mixture was blended with magnesium stearate;
  By means of direct tableting, the powder mixture was then pressed into round convex tablets of a diameter of approximately 6 mm;
  Tablets were filled into hard gelatin capsules.

Compositions as in table 1 were prepared, using Dimethyl Fumarate of three alternative particle size distributions and there dissolution profile was examined.

TABLE 2

Dissolution results for core tablets (composition 1) in phosphate buffer pH 6.8 at 100 rpm.

| | Drug Dissolved (%) | | | | | |
|---|---|---|---|---|---|---|
| Time (min) | d90 100 μm | % RSD | d90 250 μm | % RSD | d90 500 μm | % RSD |
| | | | Hard gelatin capsules | | | |
| 5 | 10.35 | 8.74 | 12.15 | 9.81 | 4.51 | 12.85 |
| 10 | 27.29 | 6.51 | 28.34 | 7.51 | 13.81 | 10.79 |
| 15 | 38.40 | 5.25 | 38.72 | 8.62 | 22.10 | 8.51 |
| 20 | 49.29 | 3.24 | 50.07 | 5.42 | 31.58 | 7.12 |
| 30 | 65.46 | 3.58 | 67.51 | 4.48 | 48.92 | 5.55 |
| 45 | 84.28 | 4.85 | 84.20 | 3.82 | 65.07 | 4.28 |
| 60 | 91.58 | 2.58 | 93.54 | 2.58 | 79.96 | 3.91 |
| 90 | 96.95 | 1.85 | 97.81 | 1.36 | 93.57 | 2.56 |
| 120 | 99.33 | 1.29 | 100.25 | 1.05 | 99.61 | 1.39 |

Based on the results, Dimethyl Fumarate of particle size distribution D90 less than 300 μm is indicated for the current invention.

Example 2

Core tablets of Composition 1 were coated with two coating layers. The first coating layer was prepared of a solution of methacrylic acid methyl methacrylate, talc, triethyl citrate and ethanol which was sprayed onto the tablet cores. The second coating layer was prepared of a dispersion of methacrylic acid ethyl acrylate and a mixture of talc and triethyl citrate in water which was then sprayed onto the previously coated tablets. The obtained enteric coated tablets were filled into hard gelatin capsules.

A range of alternative compositions on Dimethyl Fumarate 240 mg Delayed-release capsules were prepared. The weight gain of the first enteric coating layer was studied by applying a constant weight gain level for the second enteric coating.

TABLE 3

Composition of Formulation Trials 1a, 1b, 2a, 2b, 3a, 3b with alternative weight gain level on first enteric coating layer

| Core tablet | Components | | | | | |
|---|---|---|---|---|---|---|
| | Trial 1a | Trial 1b | Trial 2a | Trial 2b | Trial 3a | Trial 3b |
| | % w/w | | | | | |
| Dimethyl Fumarate | 64.92 | 64.92 | 64.92 | 64.92 | 64.92 | 64.92 |
| Microcrystalline cellulose | 29.21 | 29.21 | 29.21 | 29.21 | 29.21 | 29.21 |

TABLE 3-continued

Composition of Formulation Trials 1a, 1b, 2a, 2b, 3a, 3b with alternative weight gain level on first enteric coating layer

| Core tablet | Components Trial 1a | Trial 1b | Trial 2a % w/w | Trial 2b | Trial 3a | Trial 3b |
|---|---|---|---|---|---|---|
| Croscarmellose Sodium | 4.87 | 4.87 | 4.87 | 4.87 | 4.87 | 4.87 |
| Magnesium Stearate | 0.50 | 0.50 | 0.50 | 0.50 | 0.50 | 0.50 |
| Silica Colloidal Anhydrous | 0.50 | 0.50 | 0.50 | 0.50 | 0.50 | 0.50 |
| Total weight for uncoated tablet | 100.00 | 100.00 | 100.00 | 100.00 | 100.00 | 100.00 |
| 1st coating layer | 4.00 | 4.00 | 6.00 | 6.00 | 8.00 | 8.00 |
| Talc level (1st coating) | 0.00 | 4.40 | 0.00 | 4.40 | 0.00 | 4.40 |
| 2nd coating layer | 10.00 | 10.00 | 10.00 | 10.00 | 10.00 | 10.00 |

The impact of both enteric coating layers on final product's CQAs, acid resistance, drug release at 140 min & degradation products, was evaluated along the current studies. The results are summarized in the Table 4 below.

TABLE 4

Investigation study results of enteric coating layers on CQAs of final product.

| Formulation Trial | Acid resistance (%) | Drug release at 140 min (% of stated amount) | Degradation products (%) |
|---|---|---|---|
| Trial 1a | 11.2% | 88.0% | 2.8% |
| Trial 1b | 9.2% | 86.7% | 2.5% |
| Trial 2a | 0.7% | 84.5% | 0.15% |
| Trial 2b | 0.2% | 79.58% | 0.12% |
| Trial 3a | 0.5% | 63.0% | 0.16% |
| Trial 3b | 0.4% | 58.3% | 0.12% |
| Target | NMT 10.0% | 75.0%-85.0% | Total NMT 2.0% |

According to the results, the weight gain of 6% w/w of first enteric coating layer is adequate to provide an acid resistance in the acidic environment and prevent the hydrolysis of Dimethyl Fumarate upon contact with the aqueous coating dispersion of second layer. The talc level of 4.40% w/w is the selected level to perform a desirable dissolution profile and acid resistance. Thus, a weight gain level of 6% w/w was selected for the first enteric coating layer with 4.40% w/w of talc for Dimethyl Fumarate Delayed-release tablets provided in hard gelatin capsules.

Example 3

The second polymeric coating layer is of critical value since it rules along with the first coating layer the dissolution profile of Dimethyl fumarate and ensures the drug product acid resistance. A $2^2$ full factorial DoE with three center points was performed to optimize the level of second polymeric coating. The objective of this study was to evaluate the effect of the second polymeric coating level (weight gain) and talc level on drug release from the coated tablets. The responses studied were the acid resistance (Y1), drug release at 140 min (Y2) at 100 rpm in pH 6.8 phosphate buffer and disintegration time in pH 6.8 phosphate buffer at 37° C. The experimental results for dissolution, disintegration time and acid resistance are presented in Table 5 below.

TABLE 5

Experimental results of $2^2$ full factorial DoE

| | | Factors: Polymeric Coating Variables | | Responses | | |
|---|---|---|---|---|---|---|
| Batch No. | Pattern | A: 2nd Polymeric Coating level (% w/w) | B: Talc level (% w/w) | Y1: Acid Resistance (%) | Y2: Dissolution at 140 min (%) | Y3: Disintegration time (min) |
| 1 | +− | 10.00 | 0.00 | 1.03 | 86.52 | 13.0 |
| 2 | −+ | 6.00 | 5.00 | 3.05 | 85.65 | 12.0 |
| 3 | +− | 10.00 | 0.00 | 2.05 | 85.12 | 14.0 |
| 4 | 00 | 8.00 | 2.50 | 1.28 | 87.42 | 15.0 |
| 5 | −− | 6.00 | 0.00 | 6.51 | 86.94 | 6.0 |
| 6 | ++ | 10.00 | 5.00 | 0.00 | 85.21 | 16.0 |
| 7 | −+ | 6.00 | 5.00 | 3.52 | 84.39 | 12.0 |
| 8 | 00 | 8.00 | 2.50 | 1.02 | 86.92 | 14.0 |
| 9 | 00 | 8.00 | 2.50 | 1.97 | 89.02 | 15.0 |
| 10 | −− | 6.00 | 0.00 | 5.50 | 88.32 | 5.0 |
| 11 | ++ | 10.00 | 5.00 | 0.21 | 86.79 | 17.0 |

According to the experimental design above, the optimum polymeric coating and talc levels of the second coating were 10% w/w and 5% w/w respectively. A preferred composition is presented in Table 6 below.

TABLE 6

Preferred composition of DMF Delayed-release capsules, 120 mg & 240 mg.

| Core tablet | Components | | |
|---|---|---|---|
| | mg per tablet | mg per capsule | mg per capsule |
| Dimethyl Fumarate | 60 | 120 | 240 |
| Microcrystalline cellulose | 27 | 54 | 108 |
| Croscarmellose Sodium | 4.5 | 9 | 18 |
| Magnesium Stearate | 0.462 | 0.925 | 1.850 |
| Silica Colloidal Anhydrous | 0.462 | 0.925 | 1.850 |
| Total weight for uncoated tablet | 92.425 | 184.85 | 369.7 |
| 1st coating layer | | | |
| Methacrylic acid methyl methacrylate | 3.465 | 6.930 | 13.86 |
| Talc | 1.730 | 3.460 | 6.92 |
| Triethyl citrate | 0.345 | 0.690 | 1.38 |
| Total weight of tablet after 1st coating | 97.965 | 195.930 | 391.86 |
| 2nd coating layer | | | |
| Methacrylic acid ethyl acrylate | 24.5 | 49 | 98 |
| Talc | 1.835 | 3.670 | 7.340 |
| Triethyl Citrate | 0.610 | 1.220 | 2.440 |
| Total for coated tablet | 116 | 215.520 | 431.040 |

The preferred composition of the present invention was prepared according to the following manufacturing process:

Dimethyl fumarate was blended with croscarmellose sodium, microcrystalline cellulose and colloidal silicon dioxide;

The mixture was blended with magnesium stearate;

By means of direct tableting, the powder mixture was then pressed into round convex tablets of a diameter of approximately 6 mm;

A solution of methacrylic acid methyl methacrylate, talc, triethyl citrate and ethanol was prepared and sprayed onto the tablet cores;

A dispersion of methacrylic acid ethyl acrylate and a mixture of talc and triethyl citrate in water was prepared and sprayed onto the previously coated tablets;

The obtained enteric coated tablets were filled into hard gelatin capsules.

In order to evaluate the related substances profile of preferred dosage form of the present invention, Dimethyl Fumarate Delayed-release capsules were loaded into stability chambers and monitored with an HPLC method. Stability data upon storage at zero time, 1, 3 & 6 months under long term (25° C.±2° C./60%±5% RH), intermediate (30° C.±2° C./65%±5% RH) and accelerated storage conditions (40° C.±2° C./75%±5% RH) are presented in Table 7 below.

TABLE 7

Stability results of Dimethyl Fumarate Delayed-release capsules, 240 mg

| | Dimethyl Fumarate Delayed-release capsules, 240 mg | | | | | | | | | |
|---|---|---|---|---|---|---|---|---|---|---|
| | Zero time | 1 month | | | 3 months | | | 6 months | | |
| | | 25° C. | 30° C. | 40° C. | 25° C. | 30° C. | 40° C. | 25° C. | 30° C. | 40° C. |
| Fumaric acid (NMT 0.2%) | ND | ND | ND | ND | ND | ND | 0.01 | ND | 0.01 | 0.02 |
| MMF (NMT 0.2%) | 0.08 | 0.08 | 0.08 | 0.10 | 0.08 | 0.09 | 0.12 | 0.09 | 0.10 | 0.15 |
| Dimethyl maleate (NMT 0.2%) | ND | ND | ND | ND | ND | ND | 0.01 | ND | ND | 0.01 |
| Individual Unknown (NMT 0.2%/imp.) | 0.04 | 0.04 | 0.04 | 0.05 | 0.05 | 0.05 | 0.07 | 0.05 | 0.07 | 0.11 |
| Total (NMT 2.0%) | 0.12 | 0.12 | 0.12 | 0.15 | 0.13 | 0.14 | 0.21 | 0.14 | 0.18 | 0.29 |

Based on stability data, the related substances of preferred composition of the present invention are within specifications even in accelerated storage conditions for 6 months.

Dissolution tests were also prepared for preferred composition of the present invention and the results are presented in Table 8 below:

TABLE 8

Dissolution results of Dimethyl Fumarate Delayed-release capsules 120 mg & 240 mg at 100 rpm (paddles) in HCl 0.1N (for two hours) and phosphate buffer pH 6.8

| Time | Drug dissolved (%) | |
|---|---|---|
| (min) | 120 mg | 240 mg |
| 120 | 0.12 | 0.17 |
| 125 | 0.33 | 0.25 |
| 130 | 3.61 | 1.75 |
| 135 | 30.80 | 24.14 |
| 140 | 79.69 | 79.58 |
| 150 | 97.01 | 97.62 |
| 165 | 97.46 | 98.83 |
| 180 | 97.75 | 98.61 |
| 210 | 97.62 | 98.01 |
| 240 | 98.26 | 99.84 |

Dissolution tests also provided optimum results. Due to the tablet size difference in comparison to the originator's product the preferred composition of the present invention showed slower drug release than the originator's product resulting in more uniform drug level within the therapeutic range. The equivalence of the two products has been proved through a single-dose, four-period, two sequence, four-treatment, crossover BE study, where the geometric mean ratios of Cmax and AUC responses for test sample and reference sample are acceptable and the 90% CI relies within the range 80-125% for all PK parameters.

While the present invention has been described with respect to the particular embodiments, it will be apparent to those skilled in the art that various changes and modifications may be made in the invention without departing from the spirit and scope thereof, as defined in the appended claims.

The invention claimed is:

1. A delayed release pharmaceutical composition for oral administration comprising Dimethyl fumarate in a tablet core of diameter 5-10 mm wherein said core is coated with first and second pH-dependent gastro-resistant polymeric coating layers, and wherein the weight gain of the first polymeric coating layer is 4-8% w/w, and the weight gain of the second polymeric coating layer is 5-15% w/w.

2. A pharmaceutical composition according to claim 1, wherein the tablet core has a diameter of about 6 mm.

3. A pharmaceutical composition according to claim 1 that contains one or more coated tablet cores in a hard gelatin capsule.

4. A pharmaceutical composition according to claim 1, wherein the first coating layer comprises methacrylic acid methyl methacrylate.

5. A pharmaceutical composition according to claim 1, wherein the second coating layer comprises methacrylic acid ethyl acrylate.

6. A pharmaceutical composition according to claim 1, wherein the two polymer coatings further comprise talc at a level of 2-6% w/w.

7. A pharmaceutical composition according to claim 1, comprising Dimethyl fumarase having particle size D90 value of less than 300 microns.

8. A delayed release pharmaceutical composition for oral administration comprising Dimethyl fumarate in a tablet core of diameter 5-10 mm wherein said core is coated with first and second gastro-resistant coating layers, wherein the weight gain of the first polymeric coating layer is 4-8% w/w, and the weight gain of the second polymeric coating layer is 5-15% w/w and wherein the core exhibits an in vitro release rate of
  not more than 85 wt % Dimethyl fumarate released after 140 minutes; and
  more than 90 wt % Dimethyl fumarate released after 150 minutes.

9. A process for the preparation of a delayed release pharmaceutical composition comprising Dimethyl fumarate in a tablet core of diameter 5-10 mm wherein said core is coated with first and second gastro-resistant coating layers, which process comprises the steps of:
  Blending Dimethyl fumarate with croscarmellose sodium, microcrystalline cellulose and colloidal silicon dioxide;
  Blending the above mixture with magnesium stearate;
  Direct tableting the powder mixture into round convex tablets;
  Spraying a solution of methacrylic acid methyl methacrylate, talc, triethyl citrate and ethanol onto the tablet cores up to the desired weight gain;
  Spraying a dispersion of methacrylic acid ethyl acrylate, talc, triethyl citrate and water onto the coated tablets up to the desired weight gain;
  The appropriate amount of enteric coated tablets are filled into hard gelatin capsules;
wherein the weight gain of the first polymeric coating layer is 4-8% w/w, and that of the second polymeric coating layer is 5-15% w/w; and
wherein the Dimethyl fumarate comprises particle size D90 value of less than 300 microns.

10. The process according to claim 9, wherein the talc level is 2-6% w/w in both first and second polymer coatings.

* * * * *